(12) United States Patent  
McKay

(10) Patent No.: US 8,252,055 B2
(45) Date of Patent: Aug. 28, 2012

(54) SYNTHETIC LOADBEARING COLLAGEN-MINERAL COMPOSITES USEFUL FOR SPINAL IMPLANTS, AND METHODS OF MANUFACTURE

(75) Inventor: William F. McKay, Memphis, TN (US)

(73) Assignee: Warsaw Orthopedic, Inc., Warsaw, IN (US)

( * ) Notice: Subject to any disclaimer, the term of this patent is extended or adjusted under 35 U.S.C. 154(b) by 92 days.

(21) Appl. No.: 12/872,083

(22) Filed: Aug. 31, 2010

(65) Prior Publication Data

US 2010/0320647 A1     Dec. 23, 2010

Related U.S. Application Data

(62) Division of application No. 11/118,082, filed on Apr. 29, 2005, now Pat. No. 7,857,853.

(51) Int. Cl.
*A61F 2/44* (2006.01)
(52) U.S. Cl. .................................................. 623/17.11
(58) Field of Classification Search ...... 623/17.11–17.16
See application file for complete search history.

(56) References Cited

U.S. PATENT DOCUMENTS

| | | |
|---|---|---|
| 4,888,366 A | 12/1989 | Chu et al. |
| 5,123,925 A | 6/1992 | Smestad et al. |
| 5,702,449 A | 12/1997 | McKay |
| 5,718,012 A | 2/1998 | Cavallaro |
| 6,294,187 B1 | 9/2001 | Boyce et al. |
| 6,346,123 B1 | 2/2002 | McKay |
| 6,761,739 B2 | 7/2004 | Shepard |
| 2002/0082694 A1 | 6/2002 | McKay |
| 2004/0243242 A1 | 12/2004 | Sybert et al. |
| 2004/0259972 A1 | 12/2004 | Ringeisen et al. |
| 2005/0246021 A1 | 11/2005 | Ringeisen et al. |
| 2007/0233272 A1 | 10/2007 | Boyce et al. |

FOREIGN PATENT DOCUMENTS

WO     9909914 A1     3/1999

OTHER PUBLICATIONS

Regeneration Technologies, Inc. brochure, "Spinal Allograft Overview", Mar. 3, 2004.

*Primary Examiner* — Nicholas Woodall

(57) ABSTRACT

Described are intervertebral spinal implants that include a biocompatible load bearing composite comprised of a particulate mineral material and collagen and having a wet compressive strength of at least about 200 N/cm². The composite provides a load bearing body sized and shaped for insertion between adjacent vertebrae in a patient. The load bearing body has upper and lower surfaces configured to frictionally engage the adjacent vertebra. Also described are related methods of making and using the spinal implants, and other bone implants comprising the strong composites made available in the present invention.

16 Claims, 3 Drawing Sheets

SYNTHETIC LOADBEARING COLLAGEN-MINERAL COMPOSITES USEFUL FOR SPINAL IMPLANTS, AND METHODS OF MANUFACTURE

BACKGROUND

The present invention relates generally to spinal implants for loadbearing applications. In certain aspects, the present invention relates to synthetic spinal implants configured for placement between two adjacent vertebrae to facilitate fusion.

As further background, intervertebral discs, located between the endplates of adjacent vertebrae, stabilize the spine, distribute forces between vertebrae, and cushion vertebral bodies. A normal intervertebral disc includes a semi-gelatinous component, the nucleus pulposus, which is surrounded and confined by an outer, fibrous ring called the annulus fibrosus. In a healthy, undamaged spine, the annulus fibrosus prevents the nucleus pulposus from protruding outside the disc space.

Spinal discs may be displaced or damaged due to trauma, disease or aging. Disruption of the annulus fibrosus allows the nucleus pulposus to protrude into the vertebral canal, a condition commonly referred to as a herniated or ruptured disc. The extruded nucleus pulposus may press on a spinal nerve, which may result in nerve damage, pain, numbness, muscle weakness and paralysis. Intervertebral discs may also deteriorate due to the normal aging process or disease. As a disc dehydrates and hardens, the disc space height will be reduced leading to instability of the spine, decreased mobility and pain.

In certain instances, the only relief from the symptoms of these conditions is a discectomy, or surgical removal of a portion or all of an intervertebral disc, followed by fusion (arthrodesis) of the adjacent vertebrae. The removal of the damaged or unhealthy disc will allow the disc space to collapse. Collapse of the disc space can cause instability of the spine, abnormal joint mechanics, premature development of arthritis or nerve damage, in addition to severe pain. Pain relief via discectomy and arthrodesis requires preservation of the disc space and eventual fusion of the affected motion segments.

Historically, bone grafts have been used to fill the intervertebral space to promote fusion of the adjacent vertebrae across the disc space. In early techniques, bone material was simply disposed between the adjacent vertebrae, typically at the posterior aspect of the vertebra, and the spinal column was stabilized by way of a plate or rod spanning the affected vertebrae. Once fusion occurred, the hardware used to maintain the stability of the segment became superfluous and was a permanent foreign body. Moreover, the surgical procedures necessary to implant a rod or plate to stabilize the level during fusion were frequently lengthy and involved.

A variety of attempts have been made to develop implants for use in maintaining the disc space until complete arthrodesis is achieved. The implant must provide temporary support and allow bone ingrowth. Success of the discectomy and fusion procedure requires the development of a contiguous growth of bone to create a solid mass because the implant may not withstand the compressive loads on the spine for the life of the patient.

As examples, several metal spacers have been developed to fill the void between adjacent vertebral bodies and to promote fusion. These include hollow spinal cages that can be filled with osteogenic material, such as autograft, allograft, or osteogenic protein formulations, prior to insertion into the intervertebral space. Apertures defined in the cage communicate with the hollow interior to provide a path for tissue growth between the vertebral endplates.

Interbody spinal implants fabricated from bone have also been employed. These include for instance threaded bone dowel products and impacted spacers. Bone provides many advantages for use in fusions. It can be incorporated after fusion occurs and therefore will not be a permanent implant. Bone also allows excellent postoperative imaging because it does not cause scattering like metallic implants. Stress shielding is avoided because bone grafts have a similar modulus of elasticity as the surrounding bone.

Although an all-bone spacer provides these and other benefits, the use of bone presents several challenges. Any spacer which will be placed within the intervertebral disc space must withstand the cyclic loads of the spine. Cortical bone products may have sufficient compressive strength for such use; however, cortical bone will not promote rapid fusion. Cancellous bone is more conducive to fusion but is not biomechanically sound as an intervertebral spacer. As well, suitable allograft bone can be relatively scarce at times, potentially interrupting product supply.

In view of the background in this area, needs remain for improved and alternative intervertebral spacer implants that are fabricated from readily available materials and which have the mechanical and biological attributes necessary for loadbearing spinal applications. The present invention, in certain embodiments, is addressed to these needs.

SUMMARY OF THE INVENTION

In one embodiment, the present invention provides an intervertebral spinal implant that comprises a biocompatible load bearing composite including reconstituted fibrillar collagen and a particulate mineral. The composite has a wet compressive strength of at least about 200 Newtons per square centimeter ($N/cm^2$) and provides a body sized and configured for implant between first and second adjacent vertebrae. The body has superior and inferior surfaces configured to frictionally engage the respective adjacent vertebrae. As examples, the body can be provided in the form of a wedge, dowel or D shape, and can incorporate one or more through holes in which an osteogenic substance can be deposited and retained, either at the point of manufacture or during surgery. Advantageous frictional surfaces on the superior and inferior faces of the body can include any of a wide variety of proturbance patterns, including for example teeth, serrations or grooves.

In another embodiment, the present invention provides a method for making an intervertebral spinal implant. This method includes molding a composition comprising reconstituted fibrillar collagen and mineral particles to provide a loadbearing composite material, desirably having a wet compressive strength of at least about 200 $N/cm^2$. The composite material is shaped to provide a body for introduction between adjacent first and second vertebra; and, surface protuberances are formed on said body configured to frictionally engage the first and second vertebra. In advantageous embodiments, the body is shaped and/or the proturbances are formed during the molding procedure. As well, through holes and/or tool-engaging apertures or other adaptations can be provided in the body during molding or otherwise. The molding can be conducted under compression to provide enhanced strength and density to the inventive composite material and resulting spacers.

In another embodiment, the invention provides a bone implant material comprising a biocompatible composite including reconstituted fibrillar collagen and particulate mineral, wherein the composite has a wet compressive strength of at least about 200 N/cm$^2$, and advantageously also a bulk density of at least about 1 g/cm$^3$. In certain forms, the collagen of the composite can be crosslinked to enhance the strength of the composite material before, during and/or after a molding process used to form the composite. In other forms of the invention, the composite can be provided in the form of a molded article configured for receipt at a targeted implant site in contact with patient bone, for example at an interbody or other location within the spine. The composite can be free of bone-derived material, and in certain embodiments is free of collagenous sources other than the reconstituted fibrillar collagen. In still other embodiments, the composite can comprise both fibrillar and soluble collagen, and/or the particulate mineral can comprise a calcium phosphate mineral such as tricalcium phosphate and/or hydroxyapatite.

Further embodiments of the present invention include methods of making and using bone implant materials as described hereinabove.

Additional embodiments as well as features and advantages of the invention will be apparent from the descriptions herein.

DETAILED DESCRIPTION

Figure 1:
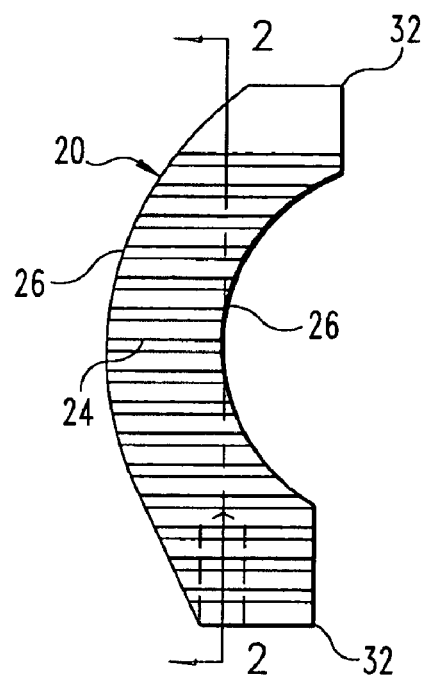
FIG. 1 is a top view of a spinal implant of the invention.

For the purposes of promoting an understanding of the principles of the invention, reference will now be made to certain embodiments thereof and specific language will be used to describe the same. It will nevertheless be understood that no limitation of the scope of the invention is thereby intended, and alterations and modifications in the illustrated implants, and further applications of the principles of the invention as illustrated herein are contemplated as would normally occur to one skilled in the art to which the invention relates.

As disclosed above, one aspect of the present invention provides intervertebral spinal implants that include a body formed with a loadbearing, biocompatible high-strength composite material comprising a particulate mineral material and collagen, wherein the loadbearing body is sized and configured for placement between first and second adjacent vertebrae, and in particular in the interbody space between the adjacent vertebrae. The implant body in certain aspects of the invention has an upper surface and a lower surface wherein each of these surfaces are configured to frictionally engage one of the pair of vertebrae. In other aspects, the invention provides for preparing and using such spinal implants.

Implants of the invention include a synthetic composite material containing a particulate mineral material and collagen. In advantageous inventive embodiments, the particulate mineral material can be a calcium phosphate ceramic. Such materials can, for example, include hydroxyapatite, tricalcium phosphate, or biphasic calcium phosphate. Other calcium-containing mineral materials may also be used, including for example calcium sulfate and bioactive glasses such as Bioglass™. These mineral components may be purchased commercially or obtained or synthesized by methods known in the art. The particulate mineral material may have any suitable particle size, including for example average particle diameters ranging from about 50 microns to about 5 millimeters (mm). In certain embodiments, the particulate mineral will have an average particle diameter of about 0.1 mm to about 3 mm.

As noted above, biphasic calcium phosphate can be used to provide the particulate mineral material in the invention. Desirably, such biphasic calcium phosphate will have a tricalcium phosphate: hydroxyapatite weight ratio of about 50:50 to about 95:5, more preferably about 70:30 to about 95:5, even more preferably about 80:20 to about 90:10, and most preferably about 85:15. A preferred particulate biphasic calcium phosphate material is known as Mastergraft™, commercially available from Medtronic Sofamor Danek, Inc. The particles in this material include curved surface features beneficial for the conduction of bone growth. Additional information regarding suitable particulate minerals and their preparation is found in WO 2004/054633 published Jul. 1, 2004 entitled Bone Substitute Material (SDGI Holdings, Inc.), which is hereby incorporated herein by reference.

A wide variety of collagen materials are suitable for combination with the particulate mineral material to form the synthetic composite material in accordance with the present invention. Naturally occurring collagens may be subclassified into several different types depending on their amino acid sequence, carbohydrate content and presence or absence of disulfide cross-links. Types I and III collagen are two of the most common sub-types of collagens. Type I collagen is present in skin, tendon and bone whereas Type III collagen is found primarily in skin. The collagen in the synthetic composite material may be obtained from skin, bone, tendon, or cartilage and purified by methods known in the art. Alternately, the collagen may be purchased commercially.

The collagen can further be atelopeptide collagen and/or telopeptide collagen. Moreover, non-fibrillar (e.g., soluble) and/or fibrillar collagen may be used. In certain embodiments of the invention, at least some fibrillar collagen is used, and in others embodiments all fibrillar collagen is used. In this regard, fibrillar collagen is collagen that has been reconstituted into its native fibrillar form. In certain preferred aspects, reconstituted fibrillar collagen having fibrils with an average length of about 0.1 mm to about 20 mm is used, more typically in the range of about 0.5 mm to about 10 mm.

The weight ratio of mineral to collagen in composites of the invention will typically be at least about 4:1, more desirably at least about 10:1. In certain inventive embodiments, the weight ratio of mineral to collagen will be at least 15:1.

Other substances can also be incorporated into the composite materials of the invention, including for example therapeutic agents such as osteogenic proteins, including BMP-2, BMP-7 and/or other bone morphogenic proteins, demineralized bone, growth factors, antibiotics, etc. In certain embodiments, the bone implant materials are intended to provide a substitute or materials sourced from bone, and can thus be free of any bone-derived materials such as cortical or cancellous bone or demineralized bone. As well, the composites can be predominantly constituted by weight of the collagen and mineral used in their preparation, for example constituted at least about 70% of the collagen and mineral, or in other embodiments at least about 90% of the collagen and mineral.

In specific embodiments, the composite material consists, or consists essentially, of the collagen and mineral materials used in its preparation.

Composite materials of the invention can also incorporate reinforcing elements, including reinforcing filaments such as strands, threads or fibers. Such reinforcing filaments or other elements can in certain embodiments be made from resorbable materials, including for example resorbable synthetic polymers or collagen. The filaments can be prepared by any suitable means including for instance extrusion, and in variants of the present invention can be relatively longer and/or greater in diameter than the fibrils of the fibrillar collagen employed, typically having a filament length in the range of about 0.5 mm to about 50 mm. These reinforcing materials can be incorporated in a mixture with the reconstituted fibrillar collagen and mineral, which is processed to provide a load bearing body as described herein.

One form of manufacturing the spinal implant involves casting the synthetic composite material in a mold. The synthetic composite material can take on the shape of the mold such as, crescent, quadrilateral, rectangular, cylindrical, or any other shape. Additionally, the surface of the mold may be smooth or may include, raised features or indentations to impart features to the spinal implant. Features from the mold can be imparted to the spinal implant as the synthetic composite material in the mold is dried or otherwise hardened. In particular aspects, a roughened or friction engaging surface can be formed on the superior surface and/or the inferior surface of the loadbearing body. More preferably, protuberances or raised portions can be imparted on the superior surface and/or the inferior surface from the mold. Such examples of protuberances or raised portions are ridges, serrations, pyramids, and teeth, to name a few.

Further, the mold can impart one or more openings extending through the loadbearing body. This opening in the loadbearing body can be sized to receive portions of a recipient's bone or a medical material such as an osteogenic formulation within the opening. Single or multiple openings can be formed in the loadbearing body. Additionally, the openings can be located anywhere within the spinal implant, for example the opening can be located in the center of the spinal implant or the opening can be a distance from the center of the spinal implant.

In another manufacturing operation, the synthetic composite material can be partially or completely machined to form a shape for the implant. Examples of such machines are lathes, drills, or other mechanical devices that can be used to shape material. The synthetic composite material can be shaped to form a crescent, a quadrilateral, a rectangle, a cylinder or any other shape that is appropriate to the intended end use. Additionally, the machines can form the roughened surface on the superior surface and/or the inferior surface of the spinal implant, tool engaging features, through-holes for osteogenic or other medical substances, etc.

In the preparation of implants of the invention, a mixture of the collagen and mineral is typically combined with a liquid to wet the material. Any suitable liquid can be used including, for example, aqueous preparations such as water, aqueous solutions such as saline (e.g. physiological saline), sugar solutions, protic organic solvents, and liquid polyhydroxy compounds such as glycerol and glycerol esters, and mixtures thereof. The liquid may, for example, constitute about 5 to about 70 weight percent of the mixed composition prior to the molding operation. Certain liquids such as water can be removed in part or essentially completely from the formed implant device using conventional drying techniques such as air drying, heated drying, lyophilization, and the like, and will be preferred.

In one mode of manufacture, a collagen-mineral mixture can be combined with a liquid, desirably with an aqueous preparation, to form a paste. Excess liquid can be removed from the paste by any suitable means, including for example by applying the paste to a liquid-permeable mold or form and draining away excess liquid.

In certain inventive embodiments, after production of the collagen-mineral composition, the composition is compressed in the production of an enhanced load bearing implant material. For example, a compressive force of at least about 1000 psi can be applied to produce composite implant materials of the invention. Typically, compressive forces of from about 1000 to about 60000 psi will be employed, more typically from about 2000 to about 20000 psi. The duration of compression can be for any suitable period of time to form the loadbearing implant material, typically ranging from several minutes to several days, more typically about 2 to 24 hours.

Before, during or after molding, including in some instances the application of compressive force to the collagen-mineral containing composition, the composition can be subjected to one or more additional operations such as heating, lyophilizing and/or crosslinking.

In this regard, crosslinking can be introduced so as to improve the strength of the formed implant. Crosslinking can be achieved by any of a variety of known methods, or combinations thereof. Such methods include for example chemical reaction, the application of energy such as radiant energy (e.g. UV light or microwave energy), drying and/or heating and dye-mediated photo-oxidation; dehydrothermal treatment; enzymatic treatment; and others.

Chemical crosslinking agents will generally be preferred, including those that contain bifunctional or multifunctional reactive groups, and which react with collagen. Chemical crosslinking can be introduced by exposing the collagen-mineral composition to a chemical crosslinking agent, either by contacting with a solution of the chemical crosslinking agent or by exposure to the vapors of the chemical crosslinking agent. As noted above, this contacting or exposure can occur before, during or after a molding operation. In any event, the resulting material can then be washed to remove substantially all remaining amounts of the chemical crosslinker if needed or desired for the performance or acceptability of the final bone implant.

Suitable chemical crosslinking agents include mono- and dialdehydes, including glutaraldehyde and formaldehyde; polyepoxy compounds such as glycerol polyglycidyl ethers, polyethylene glycol diglycidyl ethers and other polyepoxy and diepoxy glycidyl ethers; tanning agents including polyvalent metallic oxides such as titanium dioxide, chromium dioxide, aluminum dioxide, zirconium salt, as well as organic tannins and other phenolic oxides derived from plants; chemicals for esterification or carboxyl groups followed by reaction with hydrazide to form activated acyl azide functionalities in the collagen; dicyclohexyl carbodiimide and its derivatives as well as other heterobifunctional crosslinking agents; hexamethylene diisocyante; sugars, including glucose, will also crosslink collagen.

In certain aspects of the invention, the prepared composite implant materials of the invention will be relatively dense, hard materials, for example possessing a bulk density (the weight of the implant divided by its volume) of at least about 1 $g/cm^3$, more typically about 1 $g/cm^3$ to about 2 $g/cm^3$.

Additionally or alternatively, prepared composite implant materials of the invention can also possess enhanced loadbearing properties, for example exhibiting a wet compressive strength of at least about 200 N/cm$^2$, typically in the range of about 200 N/cm$^2$ to about 10000 N/cm$^2$, typically in the range of about 200 N/cm$^2$ to about 5000 N/cm$^2$, and in certain embodiments in the range of about 200 N/cm$^2$ to about 2000 N/cm$^2$. Such wet compressive strengths can be measured with the implant saturated with physiological saline, for example after being immersed in physiological saline for 12-24 hours.

The composite materials of the invention can be lyophilized after molding or other formation is completed, for example using conventional conditions such as a temperature of from about −20° to about −55° C., a vacuum of from about 150 to about 100 mTorr, for a suitable period of time, e.g. ranging from about 4 to about 48 hours.

The resulting implant can assume a determined or regular form or configuration completely or partially as a result of the molding operation. General overall forms include, for example, blocks, disks, pins, wedges, cylinders, threaded cylinders, and the like.

In certain modes of practicing the invention, the loadbearing composite of the invention can be used in the formation of a spinal implant, and in particular embodiments an interbody spinal fusion implant. For such purposes, the collagen-mineral composite can provide an implant body sized for receipt at a location between first and second adjacent vertebrae of a mammal, including a human, and can be configured to facilitate fusion of the two vertebrae. Spinal implants of advantageous embodiments of the invention include a loadbearing body having a superior or upper surface and an inferior or lower surface separated by at least one sidewall. In particular, the upper and lower surfaces can be generally planar, arcuate or combinations of these, or any other suitable configuration for contacting a surface of a first vertebrae, such as a vertebral endplate. Further, at least one of and desirably both of the upper and lower surfaces are configured to frictionally engage the first and second vertebral surfaces. The frictional engagement between the upper surface and the first vertebrae assists the loadbearing body in resisting movement after it is implanted. In one form, the upper and/or lower surface can have a generally non-smooth surface configuration to engage the surface of an adjacent vertebrae. For example, the upper and/or lower surface can be roughened, e.g., by having protuberances, raised portions, and/or grooves to frictionally engage the first vertebrae. The protuberances or raised portions could be such shapes as serrations, teeth (including directional and non-directional teeth), ridges, grooves, or pyramids, to name a few.

The sidewall of the loadbearing body in implants of the invention can be arcuate, planar or combinations of these. In certain inventive embodiments, at least one curved sidewall portion will be provided in a spinal spacer, wherein the curved sidewall portion is configured to substantially correspond to the curvature of an adjacent vertebral body.

Figure 2:
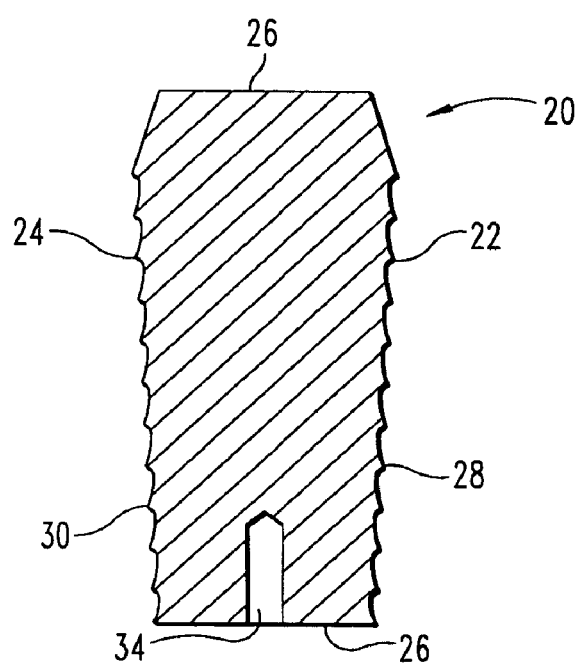
FIG. 2 is a cross-sectional view of the spinal implant shown in FIG. 1 taken along line 2-2 and viewed in the direction of the arrows.

With reference now to FIGS. 1 and 2, an illustrative spinal implant of the invention will now be described. The biocompatible loadbearing body 20 is made from a particulate mineral/collagen composite as described herein. Biocompatible loadbearing body 20 includes a superior surface 22 and an inferior surface 24 that are separated by sidewalls 26. The loadbearing 20 is shaped substantially like a 'C' shape or a crescent shape in the illustrated device. The loadbearing body 20 can be sized for placement between two adjacent vertebrae, and in particular for placement within an interbody space between first and second adjacent vertebrae. The superior surface 22 includes surface features 28. Surface features 28 can extend fully across superior surface 22 or in another form surface features 28 can extend partially across superior surface 22. In particular, the surface features 28 are a serrated shape, however other embodiments the surface features 28 can provide different frictionally-engaging shapes. The inferior surface 24 includes surface features 30. As shown, surface features 30 are serrated. As with the superior surface, surface features 30 can extend partially or fully across inferior surface 24. In general aspects of the invention, surface features 30 may be substantially similar to surface features 28 or surface features 30 may be a different shape than surface features 28.

As shown in FIGS. 1 and 2, the inferior and superior surfaces 24 and 22 each provide a substantially planar overall geometry. The sidewalls 26 are arcuate, providing an overall "C" shape to the spacer body 20. Superior surface 22 and/or inferior surface 24 can also define an angle or taper, as shown in FIG. 2. As also illustrated, a tapered portion 32 can be provided at one end of the spacer body 20, for example to provide a leading end for insertion. Loadbearing body 20 can also include an instrument hole 34 as best shown in FIG. 2. The instrument hole 34 can be configured to receive and engage a portion of medical instrument, such as an insertion instrument, to assist a medical practitioner in inserting the loadbearing body 20 between adjacent vertebrae. The instrument hole 34 can be various shapes such as, circular, rectangular, or triangular, to name a few, and can include attachment adaptations such as threads if desired.

In use, loadbearing body 20 or a pair of loadbearing bodies 20 can be inserted into the interbody space between a pair of vertebrae such that superior surface 22 substantially contacts a surface of the upper vertebrae and inferior surface 24 substantially contacts a surface of the lower vertebrae. Surface features 28 frictionally engage the surface of the upper vertebrae and surface features 30 frictionally engage the surface of the lower vertebrae. Preferably, one or more loadbearing bodies 20 are inserted in the interbody space between a pair of vertebrae in the lumbar region of the recipient's spine. Once implanted, new bone ingrowth can occur into the loadbearing body 20 thereby providing stabilization. As well, osteogenic materials such as bone (e.g. autologous patient bone), or formulations including osteogenic proteins such as bone morphogenic proteins (BMPs), including for example BMP-2 or BMP-7, can be introduced into the interbody space along with the body or bodies 20, to facilitate fusion of the adjacent vertebra.

Figure 3:
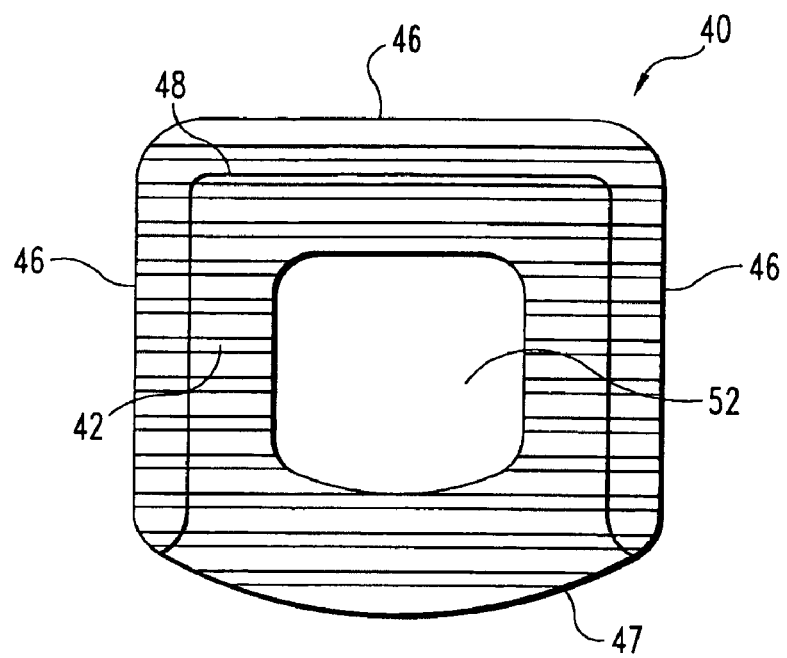
FIG. 3 is a top view of another spinal implant of the invention.
Figure 4:
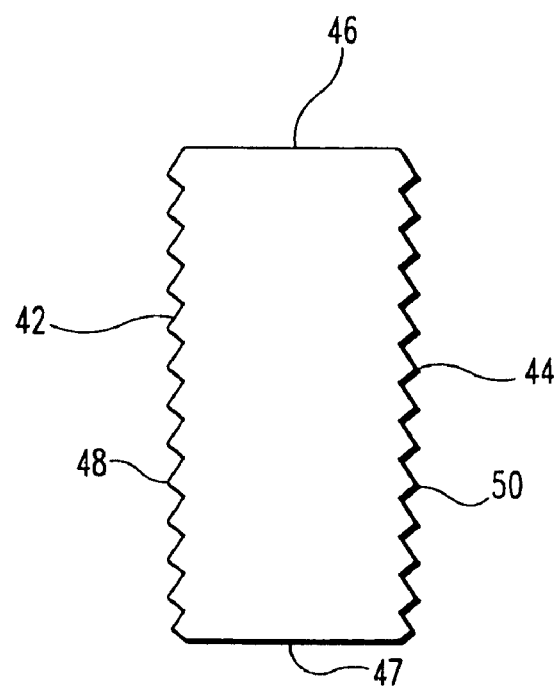
FIG. 4 is a right side view of the spinal implant shown in FIG. 3.

With reference now to FIGS. 3 and 4, another illustrative biocompatible loadbearing body 40 of the invention will now be described. The biocompatible loadbearing body 40 is formed from a collagen-mineral composite as described herein. The loadbearing body 40 can be sized for placement between a first and a second vertebrae. The loadbearing body 40 includes a superior surface 42 and an inferior surface 44 separated by planar sidewalls 46 and arcuate sidewall 47. Superior surface 42 and inferior surface 44 can be planar, arcuate, or combinations of these for contacting the surfaces of the first and second vertebrae, respectively. As illustrated, superior surface 42 and inferior surface 44 are substantially planar. The superior surface 42 includes surface features 48. The inferior surface 44 includes surface features 50. As shown in FIG. 4, the surface features 48 and surface features 50 are substantially similar and serrated in shape. As should be appreciated, the serrated shape of surface features 48 and surface features 50 can maintain the loadbearing body 40 between the pair of adjacent vertebrae and resist movement of the loadbearing body 40 from between the recipient's vertebrae. In other embodiments, surface features 48 can be shaped independently of surface features 50. As well, surface features 48 and surface features 50 can extend fully or partially across superior surface 42 and/or inferior surface 44, respectively. The loadbearing body 40 also includes an opening 52. As illustrated, the opening 52 is substantially rectangular in shape and the opening 52 generally matches the outline of the loadbearing body 40 formed by the planar sidewalls 46 and arcuate sidewall 47. The planar sidewalls 46 and the arcuate sidewall 47 as shown in FIG. 3 form a quadrilateral shape. The quadrilateral shape can be useful for implanting the loadbearing body 40 between adjacent cervical vertebrae. As shown in FIG. 3, the opening 52 is generally centrally located in the loadbearing body 40. In other forms, the opening 52 can be located anywhere within the loadbearing body 40. Further, in other forms, multiple openings 52 can be located within loadbearing body 40.

In use, the loadbearing body 40 can be placed between adjacent vertebrae such that superior surface 42 can contact a first vertebrae and surface features 48 can frictionally engage a surface of the first vertebrae. Additionally, the inferior surface 44 can contact a second vertebrae such that surface features 50 can frictionally engage a surface of the second vertebrae. Beneficially, once implanted, new bone ingrowth can occur into the loadbearing body 40 thereby providing stabilization. As well, an osteogenic substance such as patient bone or an osteogenic protein formulation, as discussed above, can be provided within central opening 52, to facilitate fusion of the adjacent vertebral bodies.

Figure 5:
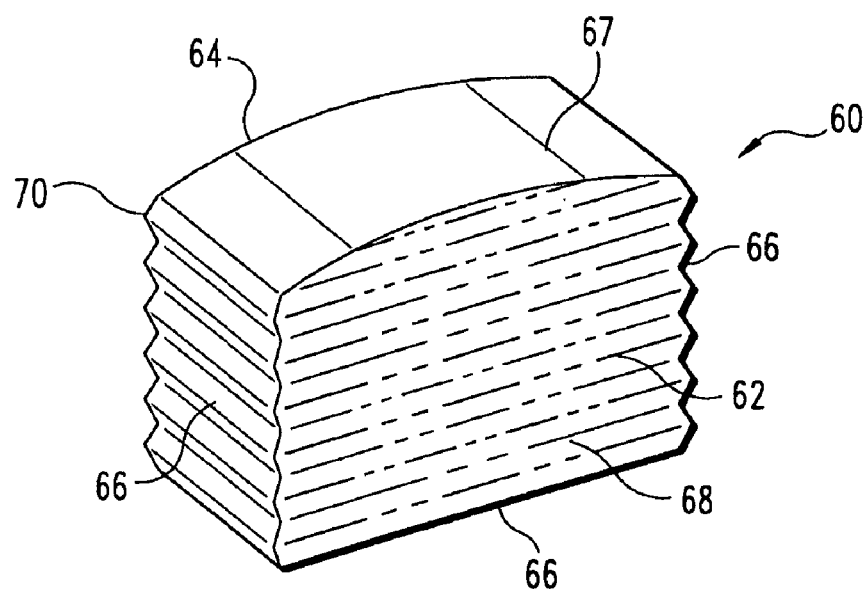
FIG. 5 is a perspective view of yet another spinal implant of the invention.

With reference to FIG. 5, another illustrative biocompatible loadbearing body 60 of the invention will be described. The biocompatible loadbearing body 60 is made from a collagen-mineral composite as described herein. The loadbearing body 60 includes a superior surface 62 separated from an inferior surface 64 by planar sidewalls 66 and arcuate sidewall 67. As shown, superior surface 62 can be generally planar for contacting a surface of the first vertebrae. Similarly, the inferior surface 64 can be generally planar for contacting a surface of the second vertebrae. As will be appreciated, in other embodiments, the superior surface 62 and/or inferior surface 64 may be arcuate, or a combination of planar and arcuate, for contacting the surface of the first and/or second vertebrae, respectively. Further, the superior surface 62 can be formed independently of the inferior surface 64. Superior surface 62 includes surface features 68 to frictionally engage the first vertebrae. As shown, the surface features 68 are raised portions shaped as serrations. The inferior surface 64 includes surface features 70 to frictionally engage a second vertebrae adjacent to the first vertebrae. The surface features 70 are also shaped as serrations. Again, surface features 68 can be shaped independently of surface features 70 in alternate inventive embodiments, and features 68 and/or 70 can provide frictionally-engaging shapes other than serrated. As shown, the loadbearing body 40 is substantially rectangular in shape, with one curved sidewall. In particular, sidewalls 66 are generally planar, whereas sidewall 67 is convexly arcuate or curved. The curved sidewall 66 can, for example, be configured to correspond to the anterior curvature of adjacent vertebra between which the loadbearing body 60 will be implanted.

In use, loadbearing body 60 can inserted in the interbody space between adjacent vertebrae such that superior surface 62 contacts a surface of the upper vertebrae and inferior surface 64 contacts a surface of the lower vertebrae. Moreover, surface features 68 can frictionally engage the surface of the upper vertebrae and surface features 70 can frictionally engage a surface of the lower vertebrae. After implanting the loadbearing body 60, new bone ingrowth can occur into and around the loadbearing body 60 thereby providing stabilization. If desired, osteogenic substances may be implanted along with body 60 to facilitate a fusion of the adjacent vertebral bodies.

Figure 6:
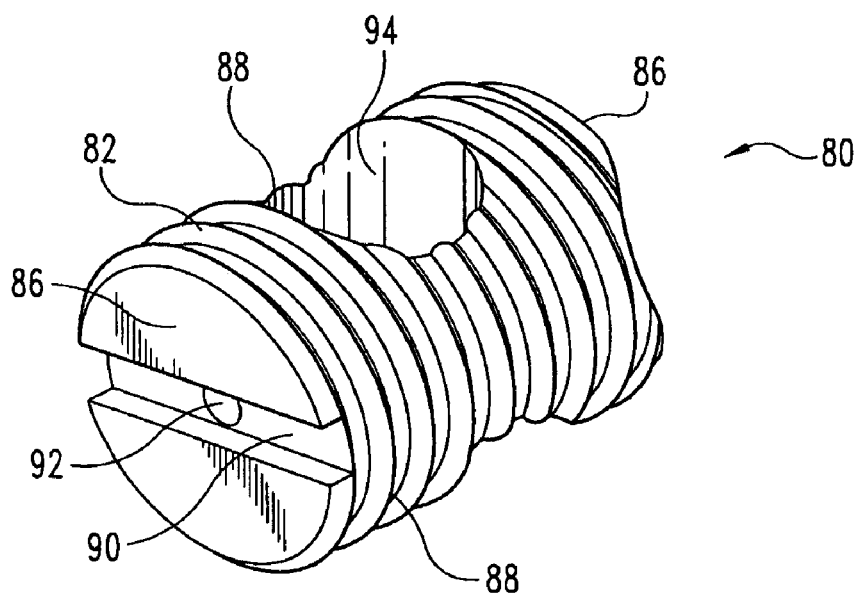
FIG. 6 is a perspective view of another spinal implant of the invention.

Referring to FIG. 6, shown is another biocompatible loadbearing body 80 according to the present invention. The biocompatible loadbearing body 80 is made from a composite material as described herein. The biocompatible loadbearing body 80 includes an outer substantially cylindrical surface 82 and a pair of endwalls 86. The outer surface 82 is arcuate for contacting a prepared (e.g. drilled) surface of a first vertebrae and a prepared surface of a second vertebrae. Further, the surface 82 includes surface features 88 for frictionally engaging both the surface of the first vertebrae and the surface of the second vertebrae. The surface features 88 as shown in FIG. 6 are generally threaded or corrugated in shape. In certain embodiments, the threaded shape of surface features 88 enables the loadbearing body 80 to be advanced as it is rotated. One endwalls 86 can include an indentation or slot 90. The indentation 90 can be sized and shaped for engaging a device for inserting the loadbearing body 80 between adjacent vertebrae. Loadbearing body 80 further includes a first opening 92 extending between the pair of endwalls 86. As shown, opening 92 is centrally located; however in other embodiments the first opening 92 can be positioned off-center. The opening 92 can be sized to receive a portion of an inserter instrument. The opening 92 is shown as circular but it will be understood that it may be shaped differently in other forms of the invention. The loadbearing body 80 can include a second opening 94 extending through the loadbearing body 80 as shown in FIG. 6. Second opening 94 can be located within the center of the loadbearing body 80 as shown or second opening 94 can be located off-center of the loadbearing body 80 in another embodiment. Second opening 94 can be sized to receive autologous patient bone or another osteogenic substance or formulation as discussed above, to facilitate bone growth through opening 94 to participate in the fusion mass.

In use, loadbearing body 80 can be inserted between a pair of vertebrae such that outer surface 82 contacts a surface of the upper vertebrae and a surface of the lower vertebrae. Surface features 88 can frictionally engage the surface of the upper vertebrae and/or the surface of the lower vertebrae such that once the loadbearing body 80 is implanted, new bone ingrowth can occur into and through the loadbearing body 80.

Generally speaking, the composite materials of the invention can be used in a variety of bone implant applications, including the preferred spinal implants and others such as in the repair of cranial defects, iliac crest back-filling, and in the repair of tibial plateau and long bone defects. Such implants can be used to treat major or minor defects in these or other bones caused by trauma, disease, or cogenital defects, for example. The implants can be inserted into a recipient's body during open surgery or during a minimally invasive surgery. Examples of minimally invasive surgery can include laproscopic techniques.

The present invention also includes spinal implant kits, wherein the kits include a spinal implant of the composite material as described herein, along with at least one additional medical device or material, such as an insertion tool, distractor, syringe, vial, needle, or other component. The components of the kits are generally packaged in a sterile condition. Such kits can likewise include instructions for use of the kit components.

While the invention has been illustrated and described in detail in the foregoing description, the same is to be considered as illustrative and not restrictive in character, it being understood that only certain embodiments have been shown and described and that all changes and modifications that come within the spirit of the invention are desired to be protected.

What is claimed is:

1. A method for making an intervertebral spinal implant, comprising:
    compression molding a composition comprising reconstituted fibrillar collagen and mineral particles to provide a loadbearing composite material having a wet compressive strength of at least about 2 MPa wherein the mineral particles have curved surface features;
    shaping said composite to provide a body for introduction between adjacent first and second vertebra; and
    forming surface protuberances on said body configured to frictionally engage said first vertebrae and said second vertebrae.

2. The method of claim 1, wherein: said composition comprises a wetting agent during said compression molding.

3. The method of claim 2, wherein said wetting agent comprises an aqueous medium.

4. The method of claim 1, wherein: said shaping occurs during said compression molding.

5. The method of claim 4, wherein: said forming occurs during said compression molding.

6. The method of claim 4, wherein: said surface protuberances comprise one or more of teeth, serrations and grooves.

7. The method of claim 4, wherein: said body is substantially cylindrical.

8. The method of claim 4, wherein: said composite material has a wet compressive strength of about 200 N/cm$^2$ to about 2000 N/cm$^2$.

9. The method of claim 8, wherein said compression molding is conducted under a pressure of at least about 1000 psi.

10. The method of claim 1, also comprising: forming at least one through hole in said body.

11. The method of claim 10, wherein said through hole is formed in said body during said compression molding.

12. The method of claim 10, wherein said through hole is machined into said body after said compression molding.

13. The method of claim 1 wherein the composite material has a bulk density of at least about 1 g/cm$^3$.

14. The method of claim 13 wherein the composite has a mineral: collagen weight ratio of at least 15:1.

15. The method of claim 14 wherein the reconstituted fibrillar collagen of the composite has an average length between 0.5 mm and 10 mm.

16. A method for making an intervertebral spinal implant, comprising: compression molding a composition comprising reconstituted fibrillar collagen and mineral particles to provide a loadbearing composite material having a wet compressive strength of at least about 2 MPa, wherein the reconstituted fibrillar collagen comprises an average length between 0.5 mm and 10 mm and the mineral particles have curved surface features; shaping said composite to provide a body for introduction between adjacent first and second vertebra; and forming surface protuberances on said body configured to frictionally engage said first vertebrae and said second vertebrae, wherein the composite comprises a mineral: collagen weight ratio of at least 15:1 and the composite comprises a bulk density of at least about 1 g/cm$^3$.

* * * * *

UNITED STATES PATENT AND TRADEMARK OFFICE
CERTIFICATE OF CORRECTION

| | | |
|---|---|---|
| PATENT NO. | : 8,252,055 B2 | Page 1 of 1 |
| APPLICATION NO. | : 12/872083 | |
| DATED | : August 28, 2012 | |
| INVENTOR(S) | : McKay | |

It is certified that error appears in the above-identified patent and that said Letters Patent is hereby corrected as shown below:

In Column 2, Line 47, delete "proturbance" and insert -- protuberance --, therefor.

In Column 2, Line 59, delete "proturbances" and insert -- protuberances --, therefor.

In Column 3, Line 25, delete "DESCRIPTION" and insert -- BRIEF DESCRIPTION --, therefor.

In Column 5, Line 24, delete "include," and insert -- include --, therefor.

In Column 6, Line 59, delete "diisocyante;" and insert -- diisocyanate; --, therefor.

In Column 10, Line 51, delete "cogenital" and insert -- congenital --, therefor.

In Column 10, Lines 54-55, delete "laproscopic" and insert -- laparoscopic --, therefor.

In Column 11, Line 17, in Claim 2, delete "wherein:" and insert -- wherein --, therefor.

In Column 11, Line 21, in Claim 4, delete "wherein:" and insert -- wherein --, therefor.

In Column 11, Line 23, in Claim 5, delete "wherein:" and insert -- wherein --, therefor.

In Column 11, Line 25, in Claim 6, delete "wherein:" and insert -- wherein --, therefor.

In Column 11, Line 27, in Claim 7, delete "wherein:" and insert -- wherein --, therefor.

In Column 11, Line 29, in Claim 8, delete "wherein:" and insert -- wherein --, therefor.

Signed and Sealed this
Twenty-third Day of October, 2012

David J. Kappos
*Director of the United States Patent and Trademark Office*